US006770042B2

(12) United States Patent
Lee

(10) Patent No.: US 6,770,042 B2
(45) Date of Patent: Aug. 3, 2004

(54) THERAPEUTIC SIGNAL COMBINATION

(76) Inventor: Richard H. Lee, 1515 Avenida Buena Vista, San Clemente, CA (US) 92672

( * ) Notice: Subject to any disclaimer, the term of this patent is extended or adjusted under 35 U.S.C. 154(b) by 110 days.

(21) Appl. No.: 09/968,578

(22) Filed: Oct. 1, 2001

(65) Prior Publication Data

US 2003/0078525 A1 Apr. 24, 2003

(51) Int. Cl.[7] .............................................. A61H 23/02
(52) U.S. Cl. ........................................ 601/47; 601/48
(58) Field of Search .............................. 601/2, 15, 46, 601/47

(56) References Cited

U.S. PATENT DOCUMENTS

| 4,306,291 A | 12/1981 | Zilm et al. |
| 5,265,619 A | 11/1993 | Comby et al. |
| 5,291,894 A | 3/1994 | Nagy |
| 5,293,879 A | 3/1994 | Vonk et al. |
| 5,361,775 A | 11/1994 | Remes et al. |
| 5,402,797 A | 4/1995 | Akiyama et al. |
| 6,193,677 B1 * | 2/2001 | Cady ............................. 601/1 |
| 6,273,864 B1 * | 8/2001 | Duarte et al. .................. 601/2 |
| 6,461,316 B1 | 10/2002 | Lee et al. |

* cited by examiner

Primary Examiner—Danton D. DeMille

(57) ABSTRACT

Multiple frequency bands with nonlinear frequency variation are combined to enhance the effectiveness of therapy delivered by an infrasonic transducer or other delivery mechanism.

17 Claims, 1 Drawing Sheet

Schematic of therapy system which combines therapeutic signals

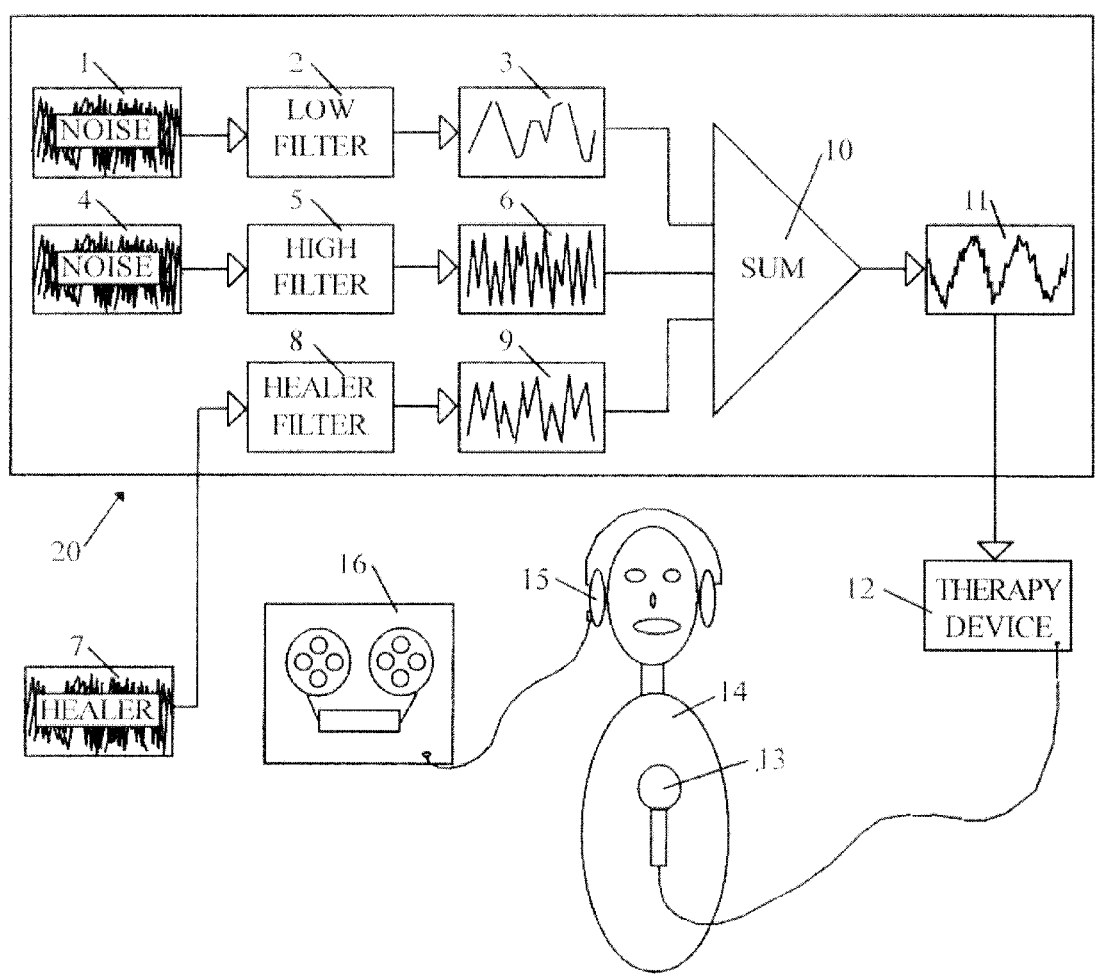
Figure 1. Schematic of therapy system which combines therapeutic signals

THERAPEUTIC SIGNAL COMBINATION

FIELD OF THE INVENTION

The present invention relates generally to therapeutic signals, and more particularly to signals induced into living bodies by infrasonic therapy devices.

BACKGROUND OF THE INVENTION

Infrasonic massagers that provide broadband sound infusion have been on the market for more than a decade, and have proven effective for a variety of therapeutic applications including pain relief, accelerated recovery, and exploring consciousness.

Previous devices that use infrasonic waves for therapy have been limited in their ability to produce signals that penetrate through body tissue to provide effective treatment. Previous devices have utilized nonlinear signal variation to produce random signals that penetrate more deeply than periodically repeating signal patterns, for example sinusoidal signals that vary rhythmically in frequency. An example of this approach is disclosed in U.S. patent application Ser. No. 08/976,100, filed on Nov. 21, 1997, by the present inventor. In that application, a method of generating and delivering an infrasonic signal with nonlinear frequency variation is disclosed wherein random noise is filtered to attenuate all frequency components that lie outside of the desired frequency band. While this approach provides an improvement in the art, more effective signal penetration is desirable.

Another problem is that when infrasonic signals are created from random noise, and particularly when multiple signals are added together, they tend to develop very high peaks, much higher than the average voltage of the signal. High voltage peaks in the signal create two problems. First, when a transducer is displaced close to its maximum displacement by high voltage peaks, the rubber diaphragm in the transducer will undergo increased stress and fail sooner. Second, as the rubber diaphragm ages, it will soften, allowing additional displacement. If the moving element in the transducer is already operating at maximum displacement, additional flexibility will allow the moving diaphragm to reach its maximum displacement and hit the magnet housing or the transducer's case, which the user will interpret as a product failure.

One solution to this problem is to reduce the amplitude of the segments of the signal that have high amplitude. However, if the peaks are simply truncated by limiting the voltage, additional frequencies will be introduced into the signal that will reduce the effectiveness of the signal. Segments may be identified and scaled by a linear factor to improve the results, but noise will be introduced at the transition points.

SUMMARY OF THE INVENTION

According to the present invention, the effectiveness of a therapeutic signal is enhanced by the synergistic application to a patient of multiple signals, each signal having a predetermined frequency spectrum and nonlinear frequency variation. The advantage of signals with nonlinear frequency variation is that they are far less predictable by the body and thus, provide more effective treatment.

According to the invention, multiple frequency bands with nonlinear frequency variation are combined to enhance the effectiveness of therapy delivered by an infrasonic transducer or other delivery mechanism.

In a preferred embodiment, a first signal in the range of 8.5 to 13.8 Hz is combined with a second lower frequency signal in the range of 1.4 and 2.9 Hz. When specific high frequency signals in the 1–2 kHz. range are combined with a low frequency signal, either a 8.5–13.8 Hz. signal or the combined signal described above, the composite signal becomes very effective. For this reason, the combination of audible bands and infrasonic bands is often highly effective at relieving pain and accelerating recovery where just the alpha infusion provides little benefit to the patient.

A second benefit of adding a high frequency signal with nonlinear frequency variation to a low frequency signal with nonlinear frequency variation is that the composite signal varies unpredictably so that the body has no way of predicting the low frequency signal and filtering it out. This substantially increases the induction of the low frequency signal into the body rhythms of the patient.

In another aspect of the invention, a therapeutic signal produced by a healer is filtered to remove all frequencies outside of a desired frequency band. In many cultures during healing rituals, healers use their voices or other sounds such as infrasonic sounds produced by their trembling hands to facilitate healing. The benefit of using a healer's signal over a synthesized signal is that the healer's signal may be more effective for some patients at relieving pain and accelerating recovery. The advantage of a filtered signal is that signals of specific frequency range are more effective than signals that cover a range of frequency bands. Thus, combining the healer's sounds with the specific frequency bandwidth of filtered technology, as disclosed herein, provides a signal that may be more effective than either a computer generated signal or the healer's recorded unfiltered signal.

The auditory signal may comprise emotionally evocative material and may be targeted specifically at known emotional disturbances like grief, depression, betrayal, or retribution. This targeted application of the auditory signal may enhance effectiveness by affecting the human levels of consciousness while the infrasonic signals activate cellular and sub-cellular responses. This programming can be spoken or played from an audio or video recording. Since buried emotions are often at the core of chronic illness and delayed healing, and can otherwise adversely affect quality of life, adding an emotionally evocative signal to infrasound therapy can be useful to facilitate healing.

In another aspect of the invention, signal peaks of an infrasonic signal are scaled without the introduction of frequencies outside the desired frequency ranges. The scaling technique disclosed herein maintains effectiveness of the therapeutic signal and improves its versatility with therapeutic signal delivery equipment. Maximum transducer displacement is reduced, increasing transducer life and decreasing the likelihood that the moving element will reach the ends of its displacement limits as the rubber diagraph ages and softens.

BRIEF DESCRIPTION OF THE DRAWINGS

Reference is made to the accompanying drawings in which are shown illustrative embodiments of the invention from which its novel features and advantages will be apparent to those of ordinary skill in the art.

FIG. 1 is a block diagram illustrating the preferred embodiment of the invention.

DETAILED DESCRIPTION OF A PREFERRED EMBODIMENT

A preferred method to generate a combined signal to be delivered to a patient will now be described with reference to FIG. 1. Signal processing apparatus 20 combines multiple discrete signals into a single composite signal output 11 to be provided to a patient 14 through a transducer 13 of a therapy device 12. In the illustrated example, two random noise signals 1 and 4 having different frequency spectra and a healer's signal 7 are filtered and combined by summer 10 to produce the composite output signal 11. Of course, the number of signals to be combined may vary from the specific illustrated example. Moreover, the healer's signal may be omitted from the signal combination.

Specifically, random noise 1 is generated and filtered by a low frequency band-pass filter 2 to produce a low frequency signal with nonlinear frequency variation within a predefined frequency range 3. Random noise 4 is generated and filtered by a high frequency band-pass filter 5 to produce a high frequency signal with nonlinear frequency variation within a pre-defined frequency range 6. A healing signal 7 from a healer is filtered by a high frequency band-pass filter 8 to produce a high frequency signal with nonlinear frequency variation within a predefined frequency range 9. The above three frequencies are combined at summer 10 to produce a composite frequency 11.

This composite frequency may be played through therapy device 12 and transducer 13 and applied to the patient 14. In addition, a recorded program 16 may be played through headphones 15 to evoke an emotional response from the patient 14 while receiving therapy.

A preferred method for combining signals is to use Matlab®, a matrix mathematics program, with built-in features for random noise generation. The Matlab program may be used to generate the random noise 1 and 4, to create and apply digital filters 2, 5 and 8, and to combine the multiple frequencies 3, 6 and 9 into composite signal 11. Digital filters 2, 5 and 8 are first prepared for the desired frequency band. The elliptical filter method is used because, while it does not provide the most uniform response within the selected range, it does provide very high attenuation outside the target range. Matlab® applies these filters to either digital input signal files 7 or white noise files 1 and 4 created in the program and adds the resulting signals together to obtain a combined signal 11. The signals are weighted according to their relative effectiveness and need. A 8.5–13.8 Hz. signal may be put in at twice the amplitude of 1.4–2.8 and 18.5–23.7 Hz. signals, and the high frequency signal is put in at 2% of the amplitude of the combined three low frequency signals. Finally, the composite signal is scaled to work in the therapy device without distortion.

This resulting signal 11 is transferred by means of a Programmable Read Only Memory ("PROM") to a therapy device 12 that delivers the desired signal to the patient 14 through a transducer 13. It should be appreciated that the computer generated signals utilized by the Matlab program could be created through analog and/or digital circuitry. It should also be appreciated that the composite signal could also be created through the use of independent circuitry.

A sample Matlab® program is provided below:

```
%
%   Composite Therapy Signal Generation Program
%   Delta+Alpha+Intuition+high frequency
%
%%%%%%%%%%%%%%%%%%%%%%%%%%%%%%%%
%
%        common parameters
%
clear;
ad_frequency_high=5000;
%   system d/a frequency
data_length=65536;
timeseconds=data_length/ad_frequency_high;
%   ffff=65536−1
%
%        produce white noise
%
fs=1000;
fs2=fs/2;
t=(0:1/fs:timeseconds)';
randomlist=rand(1,timeseconds*fs+1);
%
%        iir filter1 1.4~2.85 Hz, Delta
%
freqmin1=1.4;
freqmax1=2.85;
Wp=[freqmin1 freqmax1]/fs2;            % band pass
Ws=[freqmin1−0.5 freqmax1+3]/fs2;      % band stop
Rp=3;                                  % pass
Rs=30;                                 % stop
[n,Wn]=ellipord (Wp,Ws,Rp,Rs);
[b1,a1]=ellip (n,Rp,Rs,Wn);
%figure (1);
%freqz (b1,a1,128,1000);
signal1=filter (b1,a1,randomlist);
%
%        iir filter2 8.5~13.8 Hz, Alpha
%
freqmin2=8.5;
freqmax2=13.8;
Wp=[freqmin2 freqmax2]/fs2;            % band pass
Ws=[freqmin2−3 freqmax2+5]/fs2;        % band stop
Rp=3;                                  % pass
Rs=30;                                 % stop
[n,Wn]=ellipord (Wp,Ws,Rp,Rs);
[b2,a2]=ellip (n,Rp,Rs,Wn);
signal2=filter (b2,a2,randomlist);
%%
%        iir filter3 18.3~23.7 Hz, Intuition
%
freqmin2=18.3;
freqmax2=23.7;
Wp=[freqmin2 freqmax2]/fs2;            % band pass
Ws=[freqmin2−3 freqmax2+5]/fs2;        % band stop
Rp=3;                                  % pass
Rs=30;                                 % stop
[n,Wn]=ellipord (Wp,Ws,Rp,Rs);
[b3,a3]=ellip (n,Rp,Rs,Wn);
signal3=filter (b3,a3,randomlist);
%
%        add signal0=signal1+signal2+signal3
%
signal0=1.5*signal1+3*signal2+1.5*signal3;
%
%        Resample data: from 1000 Hz to 5000 Hz
%
mul_ad=ad_frequency_high/fs;
signal00=interp (signal0,mul_ad);
%
%        generate high frequency signal
%
freqmin (1)=985;     freqmin (2)=1192;    freqmin (3)=1369;
    freqmin (4) =1999;
freqmax (1)=1011;    freqmax (2)=1272;    freqmax (3)=1498;
    freqmax (4)=2141;
%
time_change=0.05;
%   per state continuance time (s)
number_change=4;
%   system has number_change state
number_ad=ad_frequency_high*time_change;
%   number_ad samples change state
number_frame=timeseconds*ad_frequency_high/number_ad/
    number_change;
signal4=(0:1/ad_frequency_high:timeseconds);
for f=1:1:number_frame+1
```

-continued

```
        for state=1:1:number_change
            r=rand(1,number_ad);
%
%       Random variation in each high frequency signal
%
sss=vco(r,[freqmin(state),freqmax(state)],ad_frequency_high);
        t=(f-1)*number_change*number_ad+(state-1)*number_ad+1;
        signal4(t:t+number_ad-1)=sss(1:number_ad);
        end
end
%
%       compound signal
%
signal_all(1:data_length)=signal00(1:data_length)+0.02*signal4(1
:data_length);
%
%       scaling the signal
%
max_all=max(signal_all(5000:20000));
signal_all=signal_all*(128/max_all);
%
%   store data
%
gain=1;
signal_all=signal_all*gain;
s=sum(abs(signal_all))/65536
signal_all=signal_all+128;
file='s007.dat';
[fid,message]=fopen(file,'w');
fwrite (fid,signal_all(1:65536),'char');
fclose(fid);
```

Four signals are produced and combined by this program. The first three are 1.8–2.85 Hz., 8.5–13.8 Hz., and 18.5–23.7 Hz. The fourth signal 6 is produced by switching between four high frequency bands every 0.02 seconds. Each band has nonlinear frequency variation with a new frequency randomly selected 5000 times per second. The final section of the Matlab® program, entitled "store data" writes the file to be burned onto a PROM which serves as the storage device for use in a therapy device.

An enhancement of this method involves replacing the random noise generated by the Matlab® program with a signal created by recording the voice of a healer 7 while the healer intentionally produces a healing tone. While this tone can be scaled in frequency by playing the recording slower or faster, it is preferable that the healer produces a tone in the range of the desired signal. This is accomplished by playing a tone through headphones to the healer as a reference.

To include a filtered signal from a healer, the signal from the healer is recorded and sampled at 5000 Hz. The sampled signal is digitally recorded and provided as input to the Matlab® program in place of the random signal. The healer's signal is filtered using the same digital filtering techniques as used above to produce a frequency delimited signal 9, and added to the other generated signals 10 to produce the composite signal 11. This method can be applied to either the low frequency signals from the hand of the healer, or the high frequency signals from the voice of the healer.

The emotionally evocative program is not included in the Matlab® program, but rather, may be applied separately. It is selected based on the emotional issues faced by the patient. If in written form, it is recorded on a tape recorder 16 to be played to the patient 14 through headphones 15 during the therapy session. While an auditory signal of emotionally evocative material can be included in the composite signal 11 within the Matlab® program 20 and fed through the therapy transducer 13, it is more effective for the patient to listen to a tape or watch a program on a monitor because this signal is processed by ears and brain while the infrasonic signal is processed directly by the body.

Different techniques may be utilized to make a nonlinear signal. For example, modulating a sinusoidal or other linear signal with a nonlinear signal will produce a nonlinear signal. Computer algorithms can be written to produce a wide variety of nonlinear signals.

Signals can be combined in many ways in addition to summing signals as in the low frequency signals or switching between signals, as in the high frequency signals. For example, frequency modulation, amplitude modulation, and/or phase shift modulation can be utilized. One signal may be applied magnetically, another electrically, another acoustically. As long as they are applied to the same body and evoke a response, they are still a combination of signals. The low frequency signal can easily be applied electrically to the body as a pulse train with nonlinear variation in time between pulses to provide pulses between 1.4 and 2.9 Hz. An electronic circuit may detect voltage swings of the signal from negative to positive and produce a pulse that is applied electrically through electrically conducting pads attached to the skin.

The infrasonic signals described herein may also be scaled so as to reduce undesirably high voltage peaks. According to a preferred method of signal scaling, all segments within the recorded signal that have an amplitude higher than 60% of the peak voltage are identified. For example, if the peak voltage is 10 volts, a scale factor of 0.6 applied to the peaks will bring the maximum amplitude of the entire signal down to a peak voltage of 6 volts but will leave the average amplitude relatively unchanged. In practice, overall amplitude is selected so that the signal peaks are 7.5 to 8 volts.

A scaling function utilizes a sine function as follows where frequency of the cosine function (theta) may be 9 Hz. or another frequency within the desired frequency range of the signal:

$$\text{Scaled\_signal} = \text{signal} * (1 - ((1 - \cos(\text{theta}))/2 * \text{Scale\_factor}))$$

This scaling function, "Scaled_signal," is applied to selected high-amplitude segments of the signal starting at a phase angle of 0 where its value is 1, and ending at 2π, where its value is again 1. Between these values, at π it drops to "Scale_factor," or 0.6.

Because the sine function starts at the phase angle of 0 with a very slight and gradually increasing reduction in amplitude, the effect on frequency should be low. It will be lowest if the frequency of the sine wave is within the desired frequency range. As an example, if the frequency of the scaling function is 9 Hz., then it will introduce 9 Hz. into the signal each time it is applied. A selection of scaling functions of different widths such as 2.5 Hz., 9 Hz., and 13 Hz., (all within desired frequency bands) may be applied depending on which scaling function has a width that best fits the width of the peak. In some cases it may be best to apply a scaling function 2 or 3 times to various parts of a segment to bring down the peak.

While the preferred embodiments of the devices and methods have been described, they are merely illustrative of the principles of the invention. Other embodiments and configurations may be devised without departing from the spirit of the inventions and the scope of the appended claims.

What is claimed is:

1. A therapy device comprising:
   a transducer;
   a storage medium having recorded thereon an electronic representation of a composite signal having nonlinear frequency variation, said composite signal being a combination of:

a first nonlinear signal having a first frequency spectrum, wherein said first nonlinear signal is produced by filtering a first nonlinear signal source to remove substantially all frequency signal power lying outside said first frequency spectrum, and a second nonlinear signal having a second frequency spectrum; and a signal synthesizer in communication with said transducer and said storage medium for playing back said composite signal through said transducer.

2. The therapy device of claim 1 wherein said first frequency spectrum is in the infrasonic range.

3. The therapy device of claim 1 wherein said first frequency spectrum is selected from the group consisting of 1.4–2.85 Hertz, 985–1011 Hertz, 1192–1272 Hertz, 1369–1489 Hertz, and 1999–2141 Hertz.

4. The therapy device of claim 2 wherein said second frequency spectrum includes frequencies in the audible range.

5. The therapy device of claim 2 wherein said second frequency spectrum includes frequencies in the ultrasonic range.

6. The therapy device of claim 1 wherein said first frequency spectrum includes frequencies in the audible range.

7. The therapy device of claim 6 wherein said second frequency spectrum includes frequencies in the ultrasonic range.

8. The therapy device of claim 1 wherein said first frequency spectrum is in the ultrasonic range.

9. The therapy device of claim 1, wherein said second nonlinear signal is produced by filtering a second nonlinear signal source to remove substantially all frequency signal power lying outside said second frequency spectrum.

10. The therapy device of claim 1 further comprising a third signal added into said composite signal, said third signal being derived from the voice of a healer.

11. A method of providing therapy to a patient comprising the steps of:

a) creating a first nonlinear signal having a first frequency spectrum, wherein said first nonlinear signal is produced by filtering a first nonlinear signal source to remove substantially all frequency signal power lying outside said first frequency spectrum;

b) creating a second nonlinear signal having a second frequency spectrum;

c) combining said first and second nonlinear signals into a composite signal; and d) applying said composite signal to the patient through a transducer.

12. The method of claim 11 wherein said second nonlinear signal is produced by filtering a second nonlinear signal source to remove substantially all frequency signal power lying outside said second frequency spectrum.

13. The method of claim 12 wherein said first frequency spectrum is selected from the group consisting of 1.4–2.85 Hertz, 985–1011 Hertz, 1192–1272 Hertz, 1369–1489 Hertz, and 1999–2141 Hertz.

14. The method of claim 11 further comprising the step of playing a recorded program to the patient during said step of applying said composite signal to the patient through a transducer.

15. The method of claim 11 further comprising the step of adding the filtered signal of a healer to said composite signal in said combining step.

16. A method for scaling a therapeutic signal having a predetermined frequency spectrum and nonlinear amplitude variation comprising the steps of:

a) identifying signal peaks within the predetermined frequency spectrum of the therapeutic signal;

b) selecting a scaling function to cause a greatest reduction of signal amplitude in the middle of the frequency spectrum of the therapeutic signal and minimal effect on signal amplitude at the edges of the frequency spectrum of the therapeutic signal;

c) selecting a scaling factor to be used in the scaling function; and d) applying the scaling function to the signal peaks identified during said identifying step to reduce peak values of the therapeutic signal without introducing frequencies outside of the predetermined frequency spectrum of the therapeutic signal.

17. The method of claim 16 wherein said scaling function is selected with frequency characteristics such that, when it is applied to said therapeutic signal, it induces frequencies within the predetermined frequency spectrum of said therapeutic signal.

* * * * *